(12) United States Patent
Young et al.

(10) Patent No.: US 7,801,599 B2
(45) Date of Patent: *Sep. 21, 2010

(54) TRANSDERMAL ELECTROTRANSPORT DELIVERY DEVICE INCLUDING AN ANTIMICROBIAL COMPATIBLE RESERVOIR COMPOSITION

(75) Inventors: Wendy A. Young, San Jose, CA (US); Michel J. Cormier, Mountain View, CA (US)

(73) Assignee: Alza Corporation, Vacaville, CA (US)

( * ) Notice: Subject to any disclaimer, the term of this patent is extended or adjusted under 35 U.S.C. 154(b) by 642 days.

This patent is subject to a terminal disclaimer.

(21) Appl. No.: 11/556,413

(22) Filed: Nov. 3, 2006

(65) Prior Publication Data

US 2007/0100274 A1    May 3, 2007

Related U.S. Application Data

(60) Continuation of application No. 11/084,628, filed on Mar. 18, 2005, now Pat. No. 7,761,147, which is a division of application No. 10/117,024, filed on Apr. 4, 2002, now Pat. No. 7,054,682.

(51) Int. Cl.
*A61N 1/30* (2006.01)
(52) U.S. Cl. ..................... 604/20; 604/152
(58) Field of Classification Search ............ None
See application file for complete search history.

(56) References Cited

U.S. PATENT DOCUMENTS

| | | | |
|---|---|---|---|
| 4,474,570 A | * | 10/1984 | Ariura et al. .......... 604/20 |
| 4,585,652 A | * | 4/1986 | Miller et al. .......... 604/891.1 |
| 4,603,131 A | | 7/1986 | Bernstein et al. |
| 4,927,408 A | * | 5/1990 | Haak et al. ............ 604/20 |
| 5,023,085 A | | 6/1991 | Francoeur et al. |
| 5,032,109 A | * | 7/1991 | Sibalis ................ 604/20 |
| 5,047,007 A | | 9/1991 | McNichols et al. |
| 5,080,646 A | | 1/1992 | Theeuwes et al. |

(Continued)

FOREIGN PATENT DOCUMENTS

EP    0535530    4/1993

(Continued)

OTHER PUBLICATIONS

PCT/US02/10576, PCT Search Report, 6 pgs., Aug. 12, 2002.

(Continued)

*Primary Examiner*—Nicholas D Lucchesi
*Assistant Examiner*—Pritesh Patel
(74) *Attorney, Agent, or Firm*—Michael J. Atkins

(57) ABSTRACT

A transdermal electrotransport drug delivery device having an anode, a cathode and a source of electrical power electrically connected to the anode and the cathode. At least one of the anode and the cathode includes an electrode and a reservoir comprised of a housing composed of a polymeric material and an aqueous medium in contact with the housing. The aqueous medium includes (i) a drug or an electrolyte salt or a mixture thereof, (ii) propylene glycol, and (iii) an antimicrobial agent in an amount sufficient to inhibit microbial growth in the aqueous medium. The propylene glycol prevents the antimicrobial agent from being adsorbed by other materials used in the construction of the delivery device. A process for preparing a transdermal electrotransport drug delivery device is also provided.

21 Claims, 5 Drawing Sheets

U.S. PATENT DOCUMENTS

| | | | |
|---|---|---|---|
| 5,147,296 A | | 9/1992 | Theeuwes et al. |
| 5,279,543 A | * | 1/1994 | Glikfeld et al. ............... 604/20 |
| 5,298,017 A | | 3/1994 | Theeuwes et al. |
| 5,362,307 A | | 11/1994 | Guy et al. |
| 5,434,144 A | | 7/1995 | Kasting et al. |
| 5,527,797 A | | 6/1996 | Eisenberg et al. |
| 5,533,995 A | | 7/1996 | Corish et al. |
| 5,624,415 A | | 4/1997 | Cormier |
| 5,668,120 A | | 9/1997 | Shinoda et al. |
| 5,674,871 A | | 10/1997 | Mesens et al. |
| 5,688,120 A | * | 11/1997 | Yacker et al. ................. 433/72 |
| 5,693,010 A | | 12/1997 | Ledger et al. |
| 5,766,582 A | | 6/1998 | Yuen et al. |
| 5,788,666 A | * | 8/1998 | Atanasoska ................. 604/20 |
| 5,821,237 A | | 10/1998 | Bissett et al. |
| 6,039,977 A | | 3/2000 | Venkatraman et al. |
| 6,190,691 B1 | | 2/2001 | Mak |
| 7,054,682 B2 | * | 5/2006 | Young et al. ................. 604/20 |
| 2002/0115957 A1 | | 8/2002 | Sun et al. |

FOREIGN PATENT DOCUMENTS

| | | |
|---|---|---|
| JP | 2001057967 | 3/2001 |
| WO | WO-95/27530 | 10/1995 |
| WO | WO-96/39222 | 12/1996 |
| WO | WO-96/39223 | 12/1996 |
| WO | WO-96/39224 | 12/1996 |
| WO | WO-00/25858 | 5/2000 |
| WO | WO-00/62856 | 10/2000 |
| WO | WO-00/64533 | 11/2000 |
| WO | WO-00/74772 | 12/2000 |

OTHER PUBLICATIONS

"Final Office Action mailed May 30, 2008", U.S. Appl. No. 11/084,628.

The United States Pharmacopeia 23, The National Formulary 18, (1995).

Brannan, D.K., "Cosmetic Microbiology, A Practical Handbook", CRC Press, (1997).

Brock, T.D., "Biology of Microorganisms", 3rd Edition, Prentice-Hall, Inc., (1979).

Scott, J.R., et al., "Handbook of Common Polymers", CRC Press, (1971).

Holmberg, Krister et al., "Effects on protein adsorption, bacterial adhesion and contact angle of grafting PEG chains to polystyrene", *J. Adhesion Sci. Technol.* vol. 7 No. 6, (1993), 503-517 pgs.

"USPTO Non-Final Office Action mailed Dec. 26, 2008 for U.S. Appl. No. 11/084,628, filed Mar. 18, 2005", 10 pgs.

PCT/US02/10576—International Search Report, 6 pgs.

* cited by examiner

US 7,801,599 B2

TRANSDERMAL ELECTROTRANSPORT DELIVERY DEVICE INCLUDING AN ANTIMICROBIAL COMPATIBLE RESERVOIR COMPOSITION

This application is a continuation of U.S. application Ser. No. 11/084,628, filed Mar. 18, 2005, which is a division of U.S. application Ser. No. 10/117,024, filed Apr. 4, 2002, now U.S. Pat. No. 7,054,682, which claims the benefit of U.S. Provisional Application No. 60/281,561, filed Apr. 4, 2001.

TECHNICAL FIELD

The present invention relates to a transdermal electrotransport delivery device which is designed to deliver a beneficial agent to a patient or to sample a body analyte from a patient. The device includes a reservoir that contains an antimicrobial agent that is prevented from being adsorbed by other materials used in the construction of the delivery device. The present invention further relates to a process for transdermally delivering a drug to a patient by electrotransport from a drug delivery device and a process for preparing a transdermal electrotransport delivery device. The present invention further relates to a process of making an electrotransport device.

BACKGROUND ART

The transdermal delivery of drugs, by diffusion through a body surface, offers improvements over more traditional delivery methods, such as subcutaneous injections and oral delivery. Transdermal drug delivery also avoids the hepatic first pass effect encountered with oral drug delivery. Generally the term "transdermal" when used in reference to drug delivery, broadly encompasses the delivery of an agent through a body surface, such as the skin, mucosa, nails or other body surfaces (e.g., an organ surface) of an animal.

The skin functions as the primary barrier to the transdermal penetration of materials into the body and represents the body's major resistance to the transdermal delivery of beneficial agents such as drugs. To date, efforts have concentrated on reducing the physical resistance of the skin or enhancing the permeability of the skin to facilitate the delivery of drugs by passive diffusion. Various methods of increasing the rate of transdermal drug flux have been attempted, most notably by using chemical flux enhancers.

Other approaches to increase the rates of transdermal drug delivery include the use of alternative energy sources such as electrical energy and ultrasonic energy. Electrically assisted transdermal delivery is also referred to as electrotransport. The term "electrotransport" as used herein refers generally to devices and methods which deliver an agent by electrotransport to the body as well as devices and methods which withdraw or sample body analytes from the body by "reverse" electrotransport. Examples of reverse electrotransport devices for sampling glucose (i.e. for measurement of blood glucose concentration) are disclosed in Guy et al., U.S. Pat. No. 5,362,307 and Glickfeld et al., U.S. Pat. No. 5,279,543. The delivery of a beneficial agent (e.g., a drug) or the withdrawal of a body analyte is generally through a membrane, such as skin, mucous membrane, nails or other body surfaces wherein the delivery or withdrawal is induced or aided by application of an electrical potential. For example, a beneficial agent may be introduced into the systemic circulation of a human body by electrotransport delivery through the skin. A widely used electrotransport process, referred to as electromigration (also called iontophoresis), involves the electrically induced transport of charged ions. Another type of electrotransport, referred to as electroosmosis, involves the flow of a liquid which contains the agent to be delivered, under the influence of an electric field. Still another type of electrotransport process, referred to as electroporation, involves the formation of transiently-existing pores in a biological membrane by the application of a high voltage electric field. An agent can be delivered transdermally either passively (i.e., without electrical assistance) or actively (i.e., under the influence of an electric potential). However, in any given electrotransport process, more than one of these processes, including at least some "passive" diffusion, may be occurring simultaneously to a certain extent. Accordingly, the term "electrotransport", as used herein, is given its broadest possible interpretation so that it includes the electrically induced or enhanced transport of at least one agent, which may be charged, uncharged, or a mixture thereof, whatever the specific mechanism or mechanisms by which the agent actually is transported.

Electrotransport delivery devices use at least two electrodes that are in electrical contact with some portion of the skin, nails, mucous membrane, or other surface of the body. One electrode, commonly called the "donor" electrode, is the electrode from which the agent is delivered into the body. The other electrode, typically termed the "counter" electrode, serves as a key element in the return circuit which closes the electrical circuit through the body. For example, if the agent to be delivered is positively charged, i.e., a cation, then the anodic electrode is the donor electrode, while the cathodic electrode is the counter electrode which is needed to complete the circuit. Alternatively, if an agent is negatively charged, i.e., an anion, the cathodic electrode is the donor electrode and the anodic electrode is the counter electrode. Additionally, both the anodic and cathodic electrodes may be considered donor electrodes if both anionic and cationic agent ions, or if uncharged dissolved agents, are to be delivered.

Furthermore, electrotransport devices have a donor reservoir, which is a matrix containing the beneficial agent to be delivered, positioned between the donor electrode and the patient's body surface. Preferably, electrotransport devices also have a counter reservoir, containing a physiologically-acceptable salt solution (e.g., buffered saline), positioned between the counter electrode and the patient's body surface. Examples of such reservoirs include a pouch or cavity, a porous sponge or pad, and a hydrophilic polymer or a gel matrix. Such reservoirs are electrically connected to, and positioned between, the anodic or cathodic electrodes and the body surface, to provide a source of one or more agents.

Hydrogels are particularly preferred for use as the drug and electrolyte reservoir matrices, in part, due to the fact that water is the preferred liquid solvent for use in electrotransport drug delivery due to its excellent biocompatability compared with other liquid solvents such as alcohol and glycols. Hydrogels have a high equilibrium water content and can quickly absorb water. In addition, hydrogels tend to have good biocompatibility with the skin and mucosal membranes.

Electrotransport devices also include an electrical power source such as one or more batteries. Typically, at any one time, one pole of the power source is electrically connected to the donor electrode, while the opposite pole is electrically connected to the counter electrode. Since it has been shown that the rate of electrotransport drug delivery is approximately proportional to the amount electric current flowing through the skin and the device, many electrotransport devices typically have an electrical controller that controls the voltage applied through the electrodes, thereby regulating current flow and the rate of drug delivery. These control circuits use a variety of electrical components to control the amplitude, polarity, timing, waveform shape, etc. of the electric current and/or voltage supplied by the power source. See, for example, McNichols et al., U.S. Pat. No. 5,047,007.

Electrotransport delivery devices are often stored not only at the factory but at distribution warehouses and commercial sales locations. As a result, the devices and their components must have extended shelf lives that in some instances must comply with regulatory requirements. For instance, the U.S. Food and Drug Administration has shelf life requirements of from six to eighteen months for some materials. One complicating factor in achieving an extended shelf life is that the aqueous environment in the electrode reservoirs provides an excellent medium for microorganism growth. Accordingly, an antimicrobial agent should be incorporated in the aqueous medium of the electrode reservoirs to inhibit the proliferation of microorganisms.

A number of antimicrobial agents have been used in different environments. Known antimicrobial agents (sometimes referred to as biocides) include chlorinated hydrocarbons, organometallics, halogen-releasing compounds, metallic salts, organic sulfur compounds, quaternary ammonium compounds and phenolics. Illustrative compounds include sorbic acid, benzoic acid, methylparaben and cetylpyridinium chloride. For instance, U.S. Pat. No. 5,434,144 describes topical compositions several of which include methylparaben or a cetylpyridinium salt. *Cosmetic Microbiology, A Practical Handbook*, D. Brannan, editor teaches on page 167 that alcohols (e.g., ethanol, phenoxyethanol and benzyl alcohol) and glycols (e.g. propylene glycol) can be used as preservative in food, pharmaceutical and drug products. Propylene glycol is said to exhibit a synergistic preservative effect when combined with paraben esters. *Cosmetic Microbiology, A Practical Handbook*, D. Brannan, editor, p. 167.

In the context of electrotransport devices, propylene glycol has been commonly suggested for use in plasticizing polymeric reservoir matrices. See for example U.S. Pat. No. 4,474,570. Further, propylene glycol has been used in iontophoretic device donor reservoirs to solubilize relatively hydrophobic drugs and other excipients such as stratum corneum lipid modifiers/flux enhancers. See for example U.S. Pat. Nos. 5,527,797 and 5,693,010. Additionally, U.S. Pat. No. 5,668,120 describes at column 8, lines 16-21 that preservatives, such as methylparaben and cetylpyridinium chloride (CPC), can be optionally included in the liquid vehicle of the iontophoresis medium and several of the examples of the patent include such compounds. In addition, U.S. Pat. Nos. 4,585,652 and 5,788,666 disclose that cetylpyridinium chloride can be administered by iontophoresis while U.S. Pat. No. 5,298,017 describes a number of different types of materials which can be administered by electrotransport.

DISCLOSURE OF THE INVENTION

It has been discovered that various antimicrobial agents are absorbed into the polymeric material that constitutes the housing containing the aqueous medium as well as being adsorbed by the cathodic electrode of a drug delivery device or body analyte sampling and analysis device. This absorption of an antimicrobial by these materials reduces the effectiveness of the antimicrobial agent in the aqueous medium.

Accordingly, one aspect of the present invention relates to a transdermal electrotransport drug delivery device comprised of an anode, a cathode and a source of electrical power electrically connected to the anode and the cathode, at least one of the anode and cathode having associated with it an electrode and a reservoir composed of a polymeric material which contains an aqueous medium comprised of (i) a drug or an electrolyte salt or a mixture thereof, (ii) propylene glycol and (iii) an antimicrobial agent in amounts sufficient to inhibit microbial growth in the aqueous medium, wherein propylene glycol prevents migration of the antimicrobial agent into the polymeric housing material, the cathodic or anodic electrode material and other materials that make up the construction of the drug delivery device or body analyte sampling and analysis device.

As used in the context of the present invention, the term "compatible", when used in reference to the aqueous medium, means that the antimicrobial agent in the aqueous medium will not be absorbed by any substantial amount by any material of the electrotransport device to which the aqueous medium is exposed. To determine if a particular aqueous medium formulation is compatible with the material in a device, one can prepare a solution of the aqueous medium at an appropriate concentration, immerse a sample of the material for a predetermined period of time at 25° C. and determine the amount of antimicrobial agent that is absorbed by the material by HPLC analysis of the amount of antimicrobial still in solution after the time predetermined period of time. If the amount of absorbed antimicrobial is less than 0.25 mg per gram of material, preferably less than 0.10 mg per gram of the material, most preferably less than 0.025 mg per gram of the material, the aqueous medium is considered to be compatible with the material.

In a still further aspect, the present invention relates to a process of preparing a transdermal electrotransport drug delivery device. The process comprises preparing an aqueous medium comprised of (i) a drug or an electrolyte salt or a mixture thereof, (ii) propylene glycol and (iii) an antimicrobial agent in amounts sufficient to inhibit microbial growth in the aqueous medium; and placing the aqueous medium in one or more reservoir matrices of a device comprised of an anode, a cathode and a source of electrical power electrically connected to the anode and the cathode. Preferably, either or both of the anodic reservoir and the cathodic reservoir may be composed of a polymeric reservoir matrix which contains the aforesaid aqueous medium, wherein the aqueous medium is compatible with all materials to which it is exposed In a still further aspect, the present invention relates to a process of preparing a transdermal electrotransport drug delivery device. The process comprises preparing an aqueous medium comprised of (i) a drug or an electrolyte salt or a mixture thereof, (ii) propylene glycol, and (iii) an antimicrobial agent in amounts sufficient to inhibit microbial growth in the aqueous medium; and placing the aqueous medium in the reservoir matrix of a device comprised of an anode, a cathode and a source of electrical power electrically connected to the anode and the cathode.

The aqueous medium is compatible with the material of the anode or cathode and the polymeric material of the reservoir housing. When exposed to the material of the anode or cathode, including the polymeric material of the reservoir housing, is compatible with that material.

MODES FOR CARRYING OUT THE INVENTION

Figure 1:
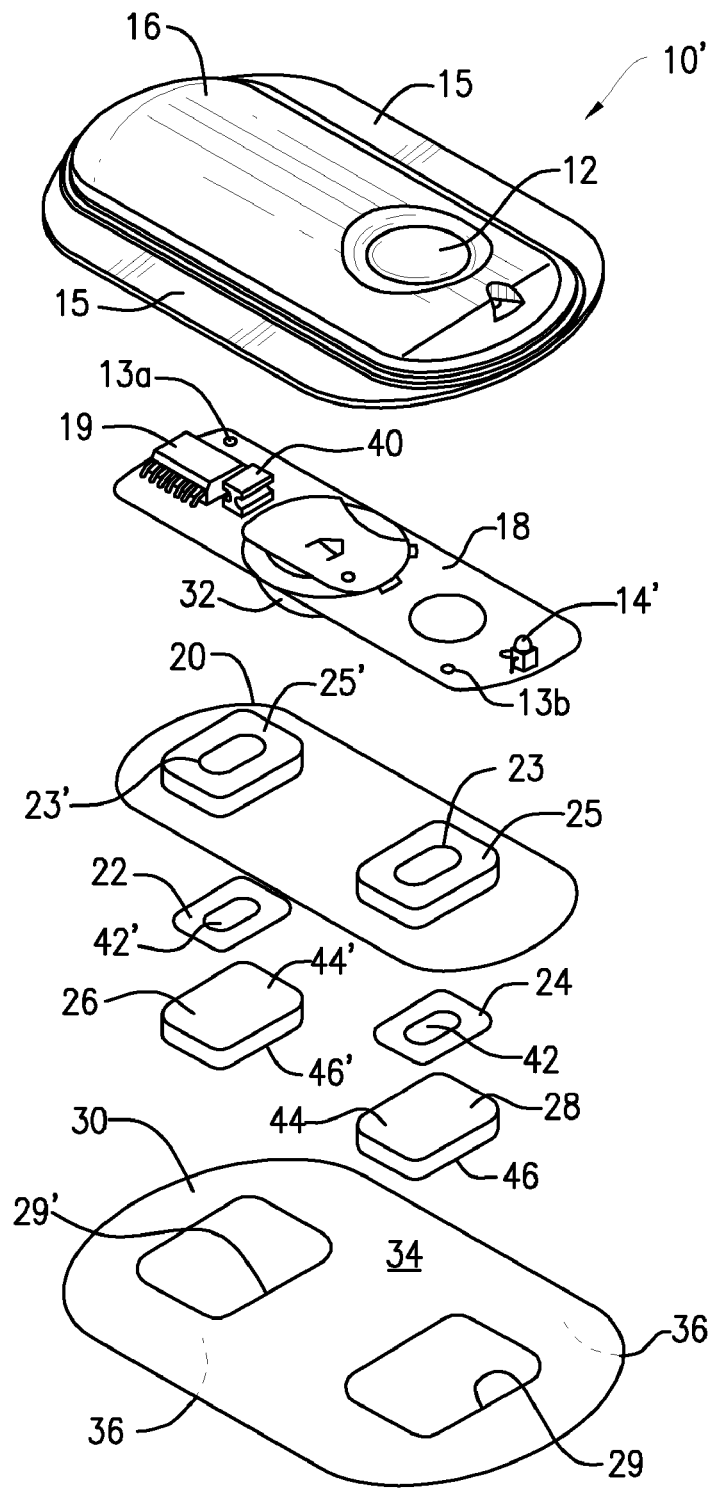
FIG. 1 is a perspective exploded view of an electrotransport drug delivery or sampling device in accordance with one embodiment of the present invention.

As noted above, one aspect of the present invention relates to a transdermal electrotransport device which is designed to deliver a drug to a patient, or to sample a body analyte from a patient, through the skin or a mucosal membrane. The transdermal electrotransport device is comprised of an anode, a cathode and a source of electrical power electrically connected to the anode and the cathode. The donor and/or counter electrode (either the anode or the cathode) includes an electrode and a reservoir comprised of a housing composed of a polymeric reservoir matrix and an aqueous medium in contact with the housing, said aqueous medium comprised of (i) a drug or an electrolyte salt or a mixture thereof, (ii) propylene glycol, and (iii) an antimicrobial agent in an amount sufficient to prevent microbial growth in the aqueous medium and wherein propylene glycol prevents migration of the antimicrobial agent into the polymer reservoir matrix, the cathodic or anodic electrode and other material to which it is exposed.

Many of the antimicrobial agents used in the present invention have poor water solubility, typically less than about 5% (w/v) and more typically less than 1% (w/v). Examples of antimicrobial agents having poor water solubility include parabens (e.g. methylparaben, ethylparaben and propylparaben), propyl gallate, butylated hydroxyanisole (BHA), butylated hydroxytoluene, t-butyl-hydroquinone, chloroxylenol, dichlorobenzyl alcohol, dehydroacetic acid, hexetidine and triclosan. These antimicrobials, when combined with a sufficient amount of propylene glycol (i.e., up to about 50 wt % and preferably about 5-40 wt % based on the total weight of the hydrated reservoir), are soluble in the reservoir but no significant fraction carries an ionic charge. Thus, the antimicrobial agent, when in solution within the reservoir, generally has a substantially neutral (i.e. no net) ionic charge. Preferably the pH of the reservoir is from about 4.0 to about 9.0 and most preferably from about 5.0 to about 8.0. However, the antimicrobial could be charged. Preferably, the antimicrobial was placed in a reservoir connected to an electrode of a polarity which did not allow the charged antimicrobial to be delivered. Because the antimicrobials are designed to inhibit microorganism growth in the reservoir, it is generally a design criteria not to deliver the antimicrobials to or through the skin. Thus, the antimicrobials tend to remain within the electrotransport reservoirs even during device operation.

Device operation inherently causes cations to migrate from the anodic reservoir, and anions to migrate from the cathodic reservoir into the skin. Examples of charged antimicrobials include benzalkonium chloride, benzethonium chloride, cetylpyridinium chloride and chlorhexidine salts.

Both these uncharged and charged antimicrobial agents are highly effective antimicrobial agents and can kill or at least inhibit the growth of a number of microorganisms, including both bacteria and fungi. The antimicrobial agent is present in an amount sufficient to inhibit microbial growth in the reservoir. In general, the reservoir contains water and propylene glycol. The reservoir contains at least about 0.005% by weight of antimicrobial. More specifically, the reservoir contains from about 0.005% to about 2% by weight of the antimicrobial and most preferably contains from about 0.01% to about 1% by weight of the antimicrobial. In calculating the weight of the aqueous medium, the weight of the propylene glycol is included but the weight of the gel matrix (to the extent that one is present) is not included.

Propylene glycol is present in the reservoir in a range from about 5 wt % to about 50 wt %. In calculating the weight of the aqueous medium, the weight of the gel matrix (to the extent that one is present) is not included.

The antimicrobial agent and propylene glycol can be used in the anodic or cathodic reservoir of substantially any transdermal electrotransport delivery or sampling device. In general, an electrotransport device provides transdermal delivery of the drug, or transdermal sampling of a body analyte such as glucose, by electrically induced or enhanced transport of the drug/analyte in a form which may be charged, uncharged, or a mixture thereof, whatever the specific mechanism or mechanisms required for the specific drug or analyte to be transported.

Electrotransport is based on utilizing electrical potential to increase the flux or rate of drug/analyte delivery compared to passive (i.e., non-electrically assisted) transdermal delivery systems which deliver a drug through the skin solely by diffusion. An especially applicable mechanism is by iontophoresis where the drug/analyte is administered or sampled in charged (ionized) form. As further discussed above, when the drug is to be administered as a cation, the drug is originally present in an anodic reservoir of the drug delivery device. On the other hand, when the drug is to be administered as an anion, the drug is originally present in a cathodic reservoir of the drug delivery device. It is also possible to have drugs in both cationic and anionic form that are simultaneously delivered from the anodic reservoir and cathodic reservoir, respectively.

Any drug which can be transdermally delivered by electrotransport can be used with the present invention including, without limitation, anti-infectives such as antibiotics and antiviral agents; analgesics such as fentanyl, sufentanil, and buprenorphine, and analgesic combinations; anesthetics; anorexics; antiarthritics; antiasthmatic agents such as terbutaline; anti-convulsants; antidepressants; antidiabetic agents; antidiarrheals; antihistamines; antiinflammatory agents; antimigraine preparations; antimotion sickness preparations such as scopolamine and ondansetron; antinauseants; antineoplastics; antiparkinson drugs; antipruritics; antipsychotics; antipyretics; antispasmodics including gastrointestinal and urinary; anticholinergics; sympathomimetics; xanthine derivatives; cardiovascular preparations including calcium channel blockers such as nifedipine; beta-agonists such as dobutamine and ritodrine; beta blockers; antiarrythmics; antihypertensives such as atenolol; ACE inhibitors such as ranitidine; diuretics; vasodilators including general, coronary, peripheral and cerebral; central nervous systems stimulants; cough and cold preparations; decongestants; diagnostics; hormones such as parathyroid hormones; hypnotics; immunosuppressives; muscle relaxants; parasympatholytics; parasympathomimetics; prostaglandins; proteins; peptides; psychostimulants; sedatives and tranquilizers.

Specific examples include baclofen, beclomethasone, betamethasone, buspirone, cromolyn sodium, diltiazem, doxazosin, droperidol, encainide, fentanyl, hydrocortisone, indomethacin, ketoprofen, lidocaine, methotrexate, metoclopramide, miconazole, midazolam, nicardipine, piroxicam, prazosin, scopolamine, sufentanil, terbutaline, testosterone, tetracaine, and verapamil.

The present invention is also useful in the controlled delivery of peptides, polypeptides, proteins, or other macromolecules difficult to deliver transdermally or transmucosally because of their size. These macromolecular substances typically have a molecular weight of at least about 300 daltons, and more typically, a molecular weight in the range of about 300 to 40,000 daltons. Examples of peptides and proteins which may be delivered using the device of the present invention include, without limitation, LHRH, LHRH analogs such as buserelin, goserelin, gonadorelin, naphrelin, naturetin, leuprolide, GHRH, GHRF, insulin, insulinotropin, heparin, calcitonin, octreotide, endorphin, TRH, NT-36 (chemical name; N-[[(s)-4-oxo-2-azetidinyl]carbonyl]L-histidyl-L-prolinamide], liprecin, pituitary hormones (e.g., HGH, HMG, HCG, desmopressin acetate), follicle luteoids, a-ANF, growth factor releasing factor (GFRF), b-MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant), and TGF-beta.

Drugs of particular interest which can be delivered by the device and process of the present invention are fentanyl and sufentanil which are synthetic opiates that are characterized by their rapid analgesic effect and short duration of action. They are extremely potent and are estimated to be 80 and 800 times, respectively, more potent than morphine. Both drugs are amine compounds and hence are weak bases whose major fraction is in cationic form in an acidic aqueous medium. When fentanyl or sufentanil is used as the drug to be administered from the anodic reservoir, the cathodic reservoir is typically substantially drug free. Examples of transdermal electrotransport fentanyl and sufentanil delivery devices are disclosed in WO 96/39222; WO 96/39223; and WO 96/39224, the disclosures of which are incorporated by reference.

The cathodic electrode and the anodic electrode are comprised of electrically conductive material such as a metal. For example, the electrodes may be formed from a metal foil, a metal screen, on metal deposited or painted on a suitable backing or by calendaring, film evaporation, or by mixing the electrically conductive material in a polymer binder matrix. Examples of suitable electrically conductive materials include carbon, graphite, silver, zinc, aluminum, platinum, stainless steel, gold and titanium. For example, as noted above, the anodic electrode may be composed of silver which is also electrochemically oxidizable. The cathodic electrode may be composed of carbon and electrochemically reducible silver chloride. Silver is preferred over other metals because of its relatively low toxicity to mammals. Silver chloride is preferred because the electrochemical reduction reaction occurring at the cathode:

$$AgCl + e^- \rightarrow Ag + Cl^-$$

produces chloride ions which are prevalent in, and non-toxic to, most animals.

Alternatively, electrodes may be formed of a polymer matrix containing a conductive filler such as a metal powder, powdered graphite, carbon fibers, or other known electrically conductive filler material. The polymer based electrodes may be made by mixing the conductive filler in a polymer matrix, preferably a mixture of hydrophilic and hydrophobic polymers. The hydrophobic polymers provide structural integrity, while the hydrophilic polymers may enhance ion transport. For example, zinc powder, silver powder, powdered carbon, carbon fibers and mixtures thereof can be mixed in a hydrophobic polymer matrix, with the preferred amount of conductive filler being within the range of about 30 to about 90 volume percent, the remainder being the polymer matrix or other inert additives.

The source of electrical power electrically connected to the anode and the cathode can be of any variety. For instance, if the counter and donor electrodes are of dissimilar metals or have different half cell reactions, it is possible for the these electrodes to comprise a galvanic couple which can generate its own electrical power. Typical materials which provide such a galvanic couple include a zinc donor electrode and a silver chloride counter electrode. Such a combination will produce a potential of about one volt. When a galvanic couple is used, the donor electrode and counter electrode are integral portions of the power generating process. Such a galvanic couple powered system, absent some controlling means, activates automatically when body tissue and/or fluids form a complete circuit with the system. There are numerous other examples of galvanic couple systems potentially useful in the present invention.

In most instances, however, it is necessary to augment the power supplied by a galvanic electrode couple. This may be accomplished with the use of a separate electrical power source. Such a power source is typically a battery or plurality of batteries, connected in series or in parallel, between the cathodic electrode and the anodic electrode such that one electrode is connected to one pole of the power source and the other electrode is connected to the opposite pole. Commonly, one or more 3 volt button cell batteries are suitable to power electrotransport devices. A preferred battery is a 3 volt lithium button cell battery.

The power source may include electronic control circuitry for controlling the operation of the electrotransport device. This control circuitry can be designed to permit the patient to manually turn the system on and off, such as with an on demand medication regimen or to turn the system on and off at some desired periodicity, for example, to match the natural or circadian patterns of the body. In addition, the control circuit can limit the number of doses that can be administered to the patient. A relatively simple controller or microprocessor can serve as the electronic control circuit and control the current as a function of time or can generate complex current waveforms such as pulses or sinusoidal waves. The control circuitry may also include a biosensor and some type of feedback system which monitors biosignals, provides an assessment of therapy, and adjusts the drug delivery accordingly. A typical example is the monitoring of the blood sugar level for controlled administration of insulin.

The aqueous medium in the anodic and cathodic reservoirs can be any material adapted to absorb and hold a sufficient quantity of liquid therein in order to permit transport of agent therethrough by electrotransport. For example, gauzes, pads or sponges composed of cotton or other absorbent fabric, both natural and synthetic, may be used. More preferably, the aqueous media are composed, at least in part, of one or more hydrophilic polymers. Hydrophilic polymers are typically preferred because water is the preferred ion transport medium and hydrophilic polymers have a relatively high equilibrium water content. Most preferably, the aqueous media in reservoirs are polymer matrices composed, at least in part, of hydrophilic polymer. Insoluble hydrophilic polymer matrices are preferred over soluble hydrophilic polymers in view of their structural properties (e.g., less swelling upon absorbing water).

The aqueous media can be a gel wherein the gel is formed of a hydrophilic polymer which is insoluble or soluble in water. Such polymers can be blended with the components in any ratio, but preferably represent from a few percent up to about 50 percent by weight of the reservoir. The polymers can be linear or crosslinked.

Suitable hydrophilic polymers include copolyesters such as HYTREL® (DuPont De Nemours & Co., Wilmington, Del.), polyvinylpyrrolidones, polyvinyl alcohol, polyethylene oxides such as POLYOX (Union Carbide Corp.), CARBOPOL® (BF Goodrich of Akron, Ohio), blends of polyoxyethylene or polyethylene glycols with polyacrylic acid such as POLYOX® blended with CARBOPOL®, polyacrylamide, KLUCEL®, cross-linked dextran such as SEPHADEX® (Pharmacia Fine Chemicals, AB, Uppsala, Sweden), WATER LOCK® (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-DiSol (FMC Corp., Philadelphia, Pa.), hydrogels such as polyhydroxyethyl methacrylate (National Patent Development Corp.), hydrophilic polyurethanes, natural gums, chitosan, pectin, starch, guar gum, locust bean gum, and the like, along with blends thereof. Of these, polyvinyl alcohols are preferred in an amount ranging from about 5% to about 35% by weight, preferably from about 19% to about 23% by weight of the contents of the reservoir. This list is merely exemplary of the materials suited for use in this invention. Other suitable hydrophilic polymers can be found in J. R. Scott & W. J. Roff, Handbook of Common Polymers (CRC Press, 1971), which is hereby incorporated by reference.

Optionally, a hydrophobic polymer may be present, to improve structural integrity. Preferably the hydrophobic polymer is heat fusible, in order to enhance the lamination to adjacent layers. Suitable hydrophobic polymers include, but are not limited to polyisobutylenes, polyethylene, polypropylene, polyisoprenes and polyalkenes, rubbers, copolymers such as KRATON®, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, 1-methyl pentanol, 2-methyl pentanol, 3-methyl pentanol, 2-ethyl butanol isooctanol, n-decanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, itaconic acid, N-branched alkyl maleamic acids, wherein the alkyl group has 10-24 carbon atoms, glycol diacrylates, and blends thereof. Most of the above-mentioned hydrophobic polymers are heat fusible.

The media in the anodic and cathodic reservoirs may be formed by blending the desired drug, electrolyte, or other component(s), with an inert polymer by such processes as melt blending, solvent casting, or extrusion. Typically, the donor reservoir medium contains a drug to be delivered, while the counter reservoir medium contains an electrolyte that is typically a biocompatible salt such as sodium chloride. For instance, the counter reservoir may contain from about 0.01% to about 1.0% by weight of an electrolyte salt, such as sodium chloride, from about 0.1% to about 1.0% by weight of citric acid or a comparable material and from about 0.1% to about 1.0% by weight of trisodium citrate dihydrate or a comparable material wherein the citric acid and the trisodium citrate dihydrate function as a buffer system. At least one, and preferably both, of the donor and counter reservoirs also contains propylene glycol and the antimicrobial agent.

In addition to the drug and electrolyte, the anodic and cathodic reservoirs may also contain other conventional materials such as inert fillers, hydrogel matrices and the like. In addition to the drug, water and the hydrogel, the donor reservoir may contain flux enhancers as disclosed in U.S. Pat. No. 5,023,085, buffers as disclosed in U.S. Pat. No. 5,624,415, resins as disclosed in WO 95/27530 and other known excipients. Specific additional components include sodium EDTA in an amount of from about 0.01% to about 1.0% by weight or L-histidine or L-histidine HCl in an amount of from about 0.1% to about 2.5% by weight.

Furthermore, one or more rate controlling membranes as disclosed in U.S. Pat. Nos. 5,080,646 and 5,147,296 may be either placed between the donor reservoir and the body surface in order to control the rate at which the agent is delivered or it may also be used to limit passive agent delivery when the power source is in an "off" mode.

Reference is now made to FIG. 1 which depicts an exemplary electrotransport device which can be used in accordance with the present invention. FIG. 1 shows a perspective exploded view of an electrotransport device 10 having an activation switch in the form of a push button switch 12 and a display in the form of a light emitting diode (LED) 14. Device 10 comprises an upper housing 16, a circuit board assembly 18, a lower housing 20, anodic electrode 22, cathodic electrode 24, anodic reservoir 26, cathodic reservoir 28 and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate).

Printed circuit board assembly 18 comprises an integrated circuit 19 coupled to discrete electrical components 40 and battery 32. Printed circuit board assembly 18 is attached to housing 16 by posts (not shown) passing through openings 13a and 13b, the ends of the posts being heated/melted in order to heat weld the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of printed circuit board assembly 18 is a battery 32, which is preferably a button cell battery and most preferably a lithium cell. Other types of batteries may also be employed to power device 10.

The circuit outputs (not shown in FIG. 1) of the circuit board assembly 18 make electrical contact with the electrodes 22 and 24 through openings 23, 23' in the depressions 25, 25' formed in lower housing, by means of electrically conductive adhesive strips 42, 42'. Electrodes 22 and 24, in turn, are in direct mechanical and electrical contact with the top sides 44', 44 of reservoirs 26 and 28. The bottom sides 46', 46 of reservoirs 26, 28 contact the patient's skin through the openings 29', 29 in adhesive 30.

Upon depression of push button switch 12, the electronic circuitry on circuit board assembly 18 delivers a predetermined DC current to the electrodes/reservoirs 22, 26 and 24, 28 for a delivery interval of predetermined length, e.g., about 10-20 minutes. Preferably, the device transmits to the user a visual and/or audible confirmation of the onset of the drug delivery, or bolus, interval by means of LED 14 becoming lit and/or an audible sound signal from, e.g., a "beeper". The drug is then delivered through the patient's skin, e.g., on the arm, for the predetermined delivery interval.

Anodic electrode 22 is preferably comprised of silver and cathodic electrode 24 is preferably comprised of carbon and silver chloride loaded in a polymer matrix material such as polyisobutylene. Both reservoirs 26 and 28 are preferably composed of polymer hydrogel materials as described herein. Electrodes 22, 24 and reservoirs 26, 28 are retained by lower housing 20. For fentanyl and sufentanil salts, the anodic reservoir 26 is the "donor" reservoir which contains the drug and the cathodic reservoir 28 contains a biocompatible electrolyte. In accordance with the present invention, either or both of the reservoirs 26 and 28 contain propylene glycol and an antimicrobial agent.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is composed of polymeric sheet material which can be easily molded to form depressions 25, 25' and cut to form openings 23, 23'. The lower housing, particularly the portions containing anodic reservoir 26 and cathodic reservoir 28, is composed of a polymeric material. Due to the action of the propylene glycol, the antimicrobial is substantially unabsorbed into the polymeric material. Suitable polymeric materials include polyethylene terephthalate, polyethylene terephthalate modified with cyclohexane dimethylol (referred to as polyethylene terephthalate glycol or PETG) that renders the polymer more amorphous, polypropylene and mixtures thereof. Preferred polymeric materials are polyethylene terephthalate and PETG which are both commercially available and PETG is most preferred. A suitable PETG is available from Eastman Chemical Products, Inc. under the designation KODAR® PETG copolyester 6763.

The assembled device 10 is preferably water resistant (i.e., splash proof) and is most preferably waterproof. The system has a low profile that easily conforms to the body thereby allowing freedom of movement at and around the wearing site. The anodic reservoir 26 and the cathodic reservoir 28 are located on the skin-contacting side of device 10 and are sufficiently separated to prevent accidental electrical shorting during normal handling and use.

The device 10 adheres to the patient's body surface (e.g., skin) by means of a peripheral adhesive 30 which has upper side 34 and body-contacting side 36. The adhesive side 36 has adhesive properties which assures that the device 10 remains in place on the body during normal user activity, and yet permits reasonable removal after the predetermined (e.g., 24 hour) wear period. Upper adhesive side 34 adheres to lower housing 20 and retains the electrodes and drug reservoirs within housing depressions 25, 25' as well as retains lower housing 20 attached to upper housing 16. The device is also usually provided with a release liner (not shown) that is initially attached to body-contacting side 36 of adhesive 30 and removed prior to attachment to the patient. The release liner is typically siliconized polyethylene ethylene terephthalate which in the presence of propylene glycol does not absorb the antimicrobial into the release liner to any significant extent. The push button switch 12 is located on the top side of device 10 and is easily actuated through clothing. A double press of the push button switch 12 within a short period of time, e.g., three seconds, is preferably used to activate the device 10 for delivery of drug, thereby minimizing the likelihood of inadvertent actuation of the device 10.

Upon activation of the switch an audible alarm signals the start of drug delivery, at which time the circuit supplies a predetermined level of DC current to the electrodes/reservoirs for a predetermined (e.g., 10 minute) delivery interval. The LED 14 remains illuminated throughout the delivery interval indicating that the device 10 is in an active drug delivery mode. The battery preferably has sufficient capacity to continuously power the device 10 at the predetermined level of DC current for the entire (e.g., 24 hour) wearing period. The integrated circuit 19 can be designed so that a predetermined amount of drug is delivered to a patient over a predetermined time and then ceases to operate until the switch is activated again and that after a predetermined number of doses has been administered, no further delivery is possible despite the presence of additional drug in the donor reservoir.

As indicated above, suitable polymeric materials that can be used to form the reservoir include polyethylene terephthalate, polyethylene terephthalate modified with cyclohexane dimethylol, polypropylene and mixtures thereof. Preferably, the material is polyethylene terephthalate or polyethylene terephthalate modified with cyclohexane dimethylol. The polymeric materials can be formed into the desired shape (e.g., the form of the lower housing) by thermoforming or any other suitable technique.

The various aspects of the present invention can be understood from the following examples and comparative examples. It is to be understood, however, that the present invention is not limited by the representative embodiments shown in the examples.

Example 1

To illustrate the antimicrobial effectiveness of the antimicrobial agent and propylene glycol formulations of the present invention, polyvinyl alcohol hydrogel formulations were made containing varying amounts of methylparaben, propylparaben and propylene glycol and tested with one mold species and one yeast species. These microorganisms are specified for the *Antimicrobial Preservative Effectiveness Test*. All percentages in this example are percent by weight unless otherwise noted. The viability of the mold and yeast inocula on the hydrogels was assayed in accordance with methods described in:

U.S. Phamacopeia 23 <51> *Antimicrobial Preservatives-Effectiveness;*

British Pharmacopoeia (BP) Appendix XVI C *Efficacy of Antimicrobial Preservation*; and European Pharmacopoeia (EP) VIII.15 *Efficacy of Antimicrobial Preservation.*

The microorganisms used in the inocula were as follows:
*Candida albicans* ATCC 10231
*Aspergillus niger* ATCC 16404

The formulations used in the tests are as follows:

| Formulation 1 (5 wt % propylene glycol): | |
|---|---|
| USP Purified Water | 71.80% |
| washed polyvinyl alcohol | 23.00% |
| propylene glycol | 5.00% |
| methylparaben | 0.18%, |
| propylparaben | 0.02% |

The formulation had a pH of about 5.0

| Formulation 2 (10 wt % propylene glycol): | |
|---|---|
| USP Purified Water | 67.00% |
| washed polyvinyl alcohol | 23.00% |
| propylene glycol | 10.00% |
| methylparaben | 0.18% |
| propylparaben | 0.02% |

The formulation had a pH of about 5.0

| Comparative Formulation 3 (Control—No parabens): | |
|---|---|
| USP Purified Water | 67.00% |
| washed polyvinyl alcohol | 23.00% |
| propylene glycol | 10.00% |

The formulation had a pH of 5.0

Preparation of Hydrogels

Preparation of Formula 1

Samples of hydrogel formulation of Formulation 1 were prepared by adding into a 250 ml jacketed glass beaker 71.80 g USP purified water; 5.00 g propylene glycol; 0.18 g methylparaben; and 0.02 g propylparaben. The resulting mixture was stirred for 5 to 10 minutes with a glass stirring rod. Washed polyvinyl alcohol, 23.00 g, was added to the beaker. A rubber stopper was equipped with a thermocouple thermometer and a glass stirring rod with a Delrin paddle and was inserted into the mouth of the beaker. The mixture was warmed to 90 to 95° C. while stirring and held at that temperature for approximately 60 minutes. The hot poly(vinyl alcohol) solution was cooled to approximately 60° C. and transferred into a 60 ml polypropylene syringe. The polypropylene syringe and contents were placed in an aluminum block heater previously warmed to 60° C. and dispensed into 1.0 cm$^2$×$^1$/$_{16}$ inch thick polyethylene housing with adhesive on both sides covered by a release liner. After dispensing the housing was subjected to freeze-thaw processing.

Samples of the hydrogel formulations based upon Formulation 2 (10 wt % propyl paraben) and Formulation 3 (0 wt % propyl paraben) were prepared using the same technique except that the amount of the respective materials were increased, decreased or eliminated entirely.

Preparation of the Yeast and Mold Inocula:

The following media were used in the tests:
Sabouraud Dextrose Agar (SDA), Difco Code No. 0305-17-3, or equivalent
Trypticase Soy Broth, BBL No. 11768 or equivalent with the addition of 0.1% Polysorbate 80, BBL No. 11925 or equivalent.

Suspensions of inocula were made for each of the challenge organisms in accordance with a standard procedure and only cultures with less than five passes were used. The suspensions were adjusted to approximately $1.0 \times 10^8$ colony forming units (CFU)/ml in accordance with a standard procedure. Immediately before inoculation onto the test hydrogels, the inocula concentrations were confirmed by Pour Plate Method (see the description provided in the US Pharmacopoeia 1995 and the publication *Biology of Microorganisms*, 3$^{rd}$. Ed. 1979, the contents of which are incorporated by reference). The Pour Plate Method used Sabouraud Dextrose Agar (SDA) for yeast and mold. The SDA plates were inoculated with *C. Albicans* and *A. Niger* species and then incubated at 20-25° C. for 5-7 days. After incubation, the colonies were enumerated. The average colonies counted between the triplicate plates was multiplied by the dilution factor to obtain the number of organisms per system.

Inoculation Procedure:

To test the various hydrogel samples, protective release liners were removed under aseptic conditions, and three gel-filled foam housings were placed in a sterile petri dish. Each hydrogel was inoculated with 3 μL of the microorganism suspension (approximately $3.0 \times 10^5$ CFU/system). Immediately after inoculation, the release liner was replaced and the inoculated hydrogel was placed in a foil pouch, which was sealed using a heat sealer. Sealed packages containing the inoculated systems were incubated at 20-25° C. Three inoculated hydrogels were recovered at 1, 2, 7, 14, 22, and 28 days after inoculation. This procedure was repeated for each of the two microorganisms tested.

Evaluation of Hydrogel Test Samples:

In order to evaluate the samples, each hydrogel was extracted by first placing it into a screw-capped tube containing 20 ml of TSP with 0.1% Polysorbate 80. Each tube was shaken for 30 minutes at 200 rpm and then vortexed for 1 minute at high speed. Using the Pour Plate method, serial dilutions of the extract were plated on SDA for the yeast and mold. The plates were then incubated and enumerated in the manner discussed above.

Figure 2:
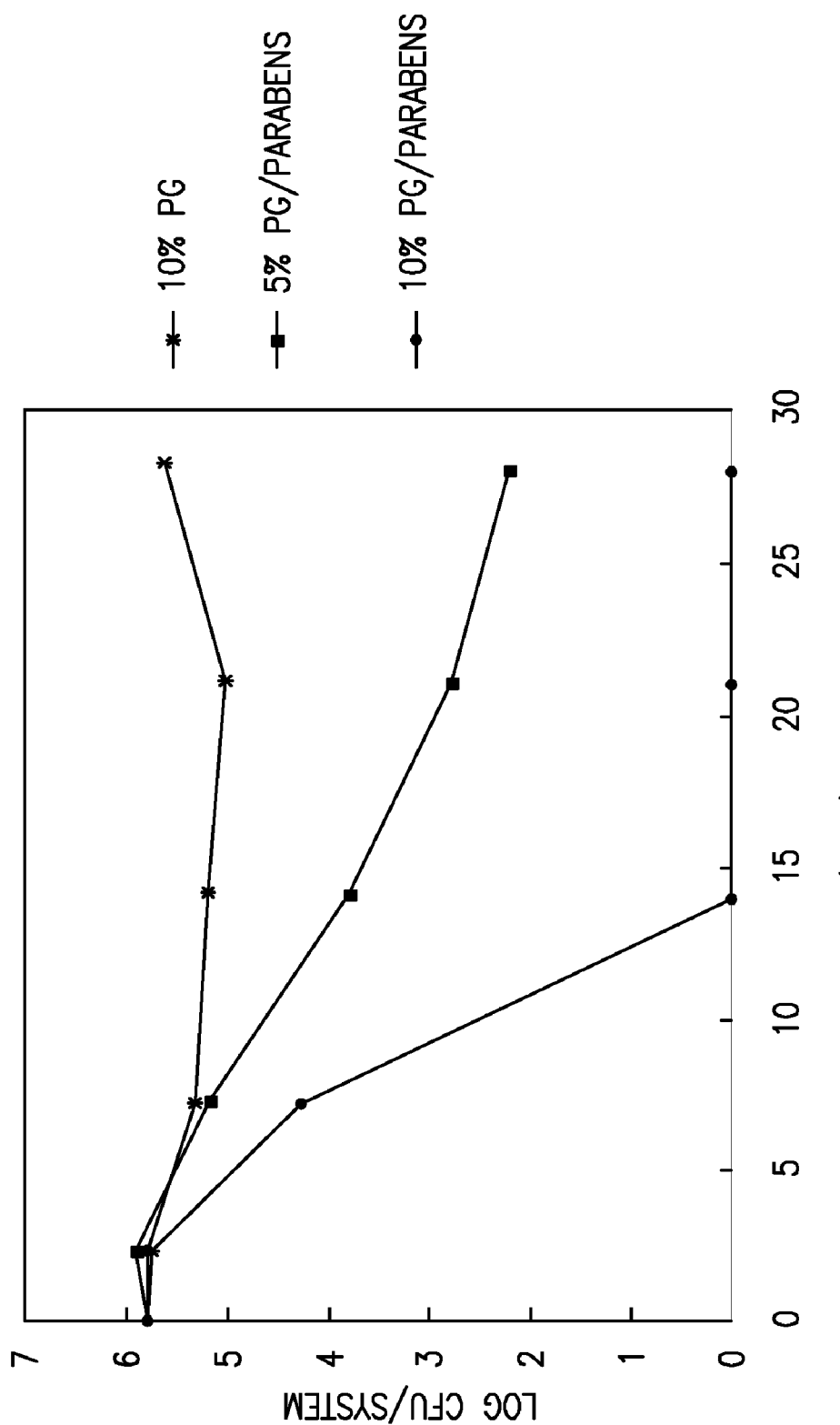
FIG. 2 is a graph of log of *C. Albicans* colony forming units on polyvinyl alcohol gels versus time.
Figure 3:
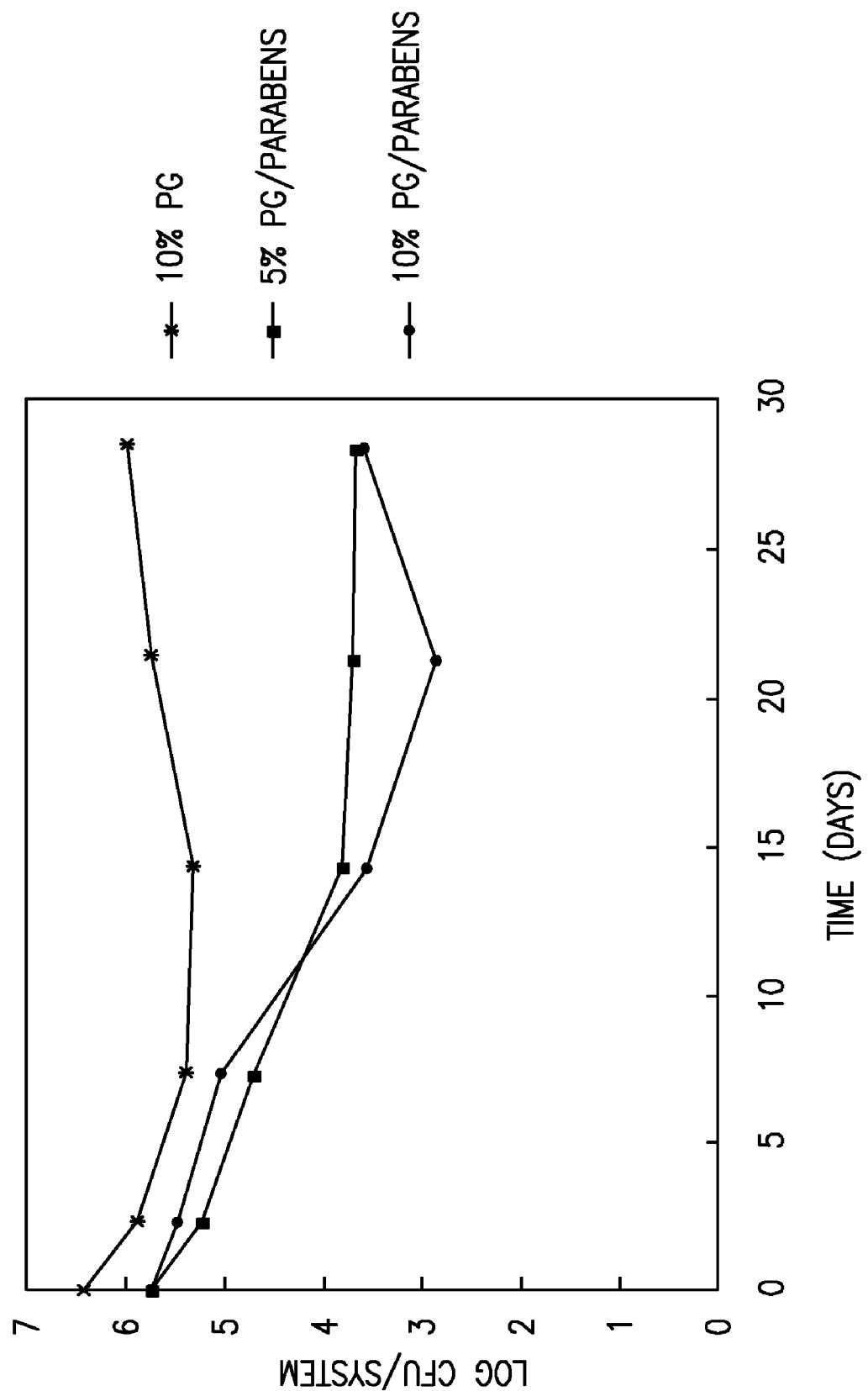
FIG. 3 is a graph of log *A. Niger* colony forming units on polyvinyl alcohol gels versus time.

Results:

The results of the tests are set forth in FIG. 2 (*C. Albicans*) and FIG. 3 (*A. Niger*) and indicate that the hydrogel formulations containing propylene glycol and parabens meet the antimicrobial preservative efficacy requirement as stated in the US Pharmacopoeia 23 Microbiological Tests <51> Antimicrobial Preservatives-Effectiveness. The efficacy requirement is that the concentrations of viable yeast and molds remain at or below the initial concentrations though out the 28-day study.

At all tested concentrations of propylene glycol and parabens, the viable microbial counts of all the challenge mold and yeast were reduced by at least 2 logs at Day 28 of the study.

Further analysis of the experimental results indicate that the hydrogel formulations containing propylene glycol and parabens also satisfy the antimicrobial preservative requirements for topical preparations as stated in the British Pharmacopoeia which are that the viable yeast and mold count was reduced by a minimum of two logs at the 14-day time point with no increase in the challenge fungi at the 28 day point.

In addition, the hydrogel formulations also satisfy the antimicrobial preservative requirements for topical preparations as stated in the Criteria A of the European Pharmacopoeia which are that the viable yeast and mold count was reduced by a minimum of two logs at the day-14 time point with no increase of the challenge fungi at the day-28 time point.

It should be noted that the antimicrobial efficacy of the parabens in each of the two tests tended to be greater in those preparations which had the higher propylene glycol concentration.

Example 2

Figure 4:
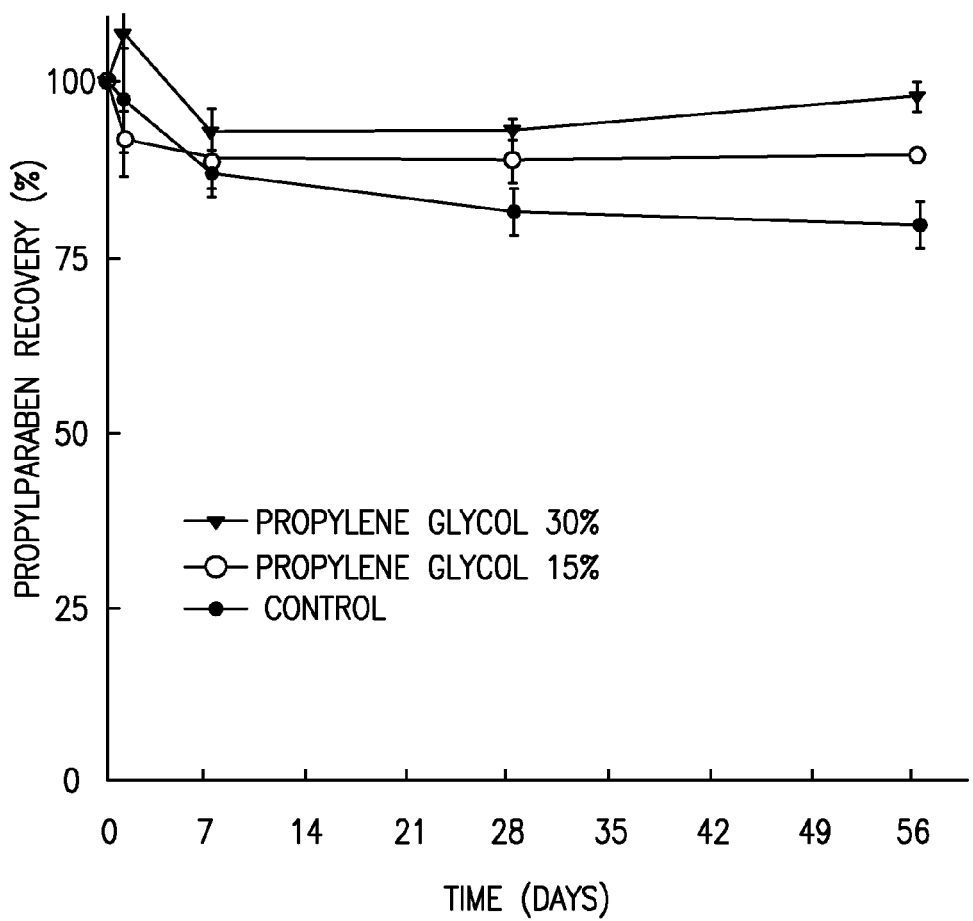
FIG. 4 is a graph of the recovery of propylparaben versus time in test solutions having 0, 15, or 30 wt % propylene glycol showing the effect of propylene glycol on the concentration of parabens in a reservoir solution containing PETG, the material used for the reservoir housing.
Figure 5:
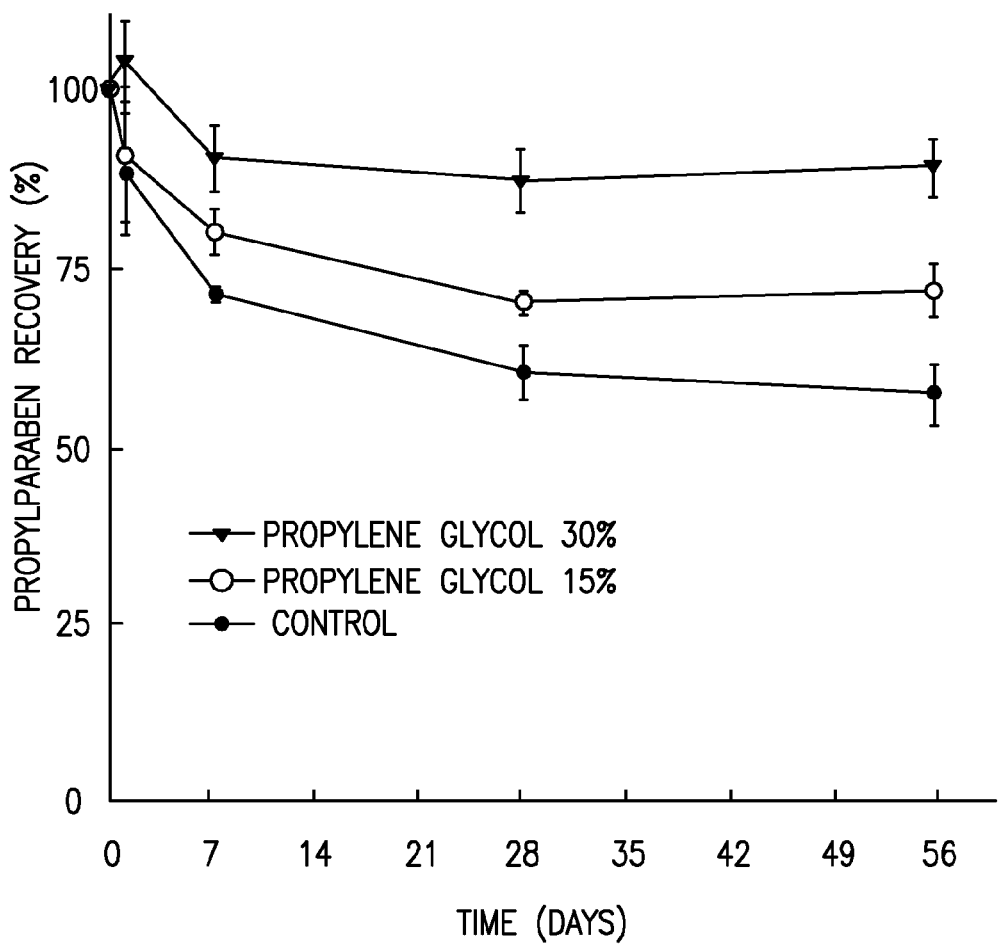
FIG. 5 is a graph of the recovery of propylparaben versus time in test solutions having 0, 15, or 30 wt % propylene glycol showing the effect of propylene glycol on the concentration of parabens in a reservoir solution containing cathodic electrode material.

Experiments were also performed to show that propylene glycol helps prevent the loss of propylparaben from the reservoir solution. The results of these tests are shown in FIGS. 4 and 5 with details of the tests described below 11.

The tests were performed using a test solution that is similar to that used to hydrate the gel matrix. This test solution was exposed to two types of material. The first material was polyethylene terephthalate glycol (PETG) which is the material used to make the reservoir housing. The second material was the material used to make the cathode electrode, which is a polyisobutylene/AgCl/carbon black formulation.

The base test solution was 0.18 wt % methylparaben and 0.02 wt % propylparaben in a citrate buffer with a pH of 5.0. There were three variations of the solution that were tested. The first test solution was the same as the base solution and specifically had no propylene glycol added. The second variation was the base solution that was also 15 wt % of propylene glycol and the third variation was the base solution that was also 30 wt % of propylene glycol.

Each of the three solutions was tested by exposing each of the two test materials to 3.0 mls of each of the three test solution in separate 5.0 ml vials that were kept sealed at 25° C. for 56 days. The actual mass of each of the test material samples placed in the vials was selected to have a surface area such that the ratio of surface area of material to volume of solution in the test samples approximated the ratio of surface area of material to volume of solution that exists in the actual reservoirs. Samples that were 200 μL in size were taken from each vial at days 0, 1, 7, 28 and 56. The samples were analyzed for the presence of methylparaben and propylparaben by HPLC. Triplicates of each of the six possible combinations of three test solutions and two test materials were tested. Data from the triplicates were normalized to the initial concentration and plotted as mean±sem as shown in FIGS. 4 and 5.

Although the present invention has been described with reference to certain preferred embodiments, it is apparent that modifications and variations thereof may be made by those skilled in the art without departing from the scope of the invention as defined by the following claims.

What is claimed is:

1. A transdermal electrotransport drug delivery or body analyte sampling device comprised of an anode, a cathode and a source of electrical power electrically connected to the anode and the cathode, at least one of the anode and the cathode including an electrode and a reservoir comprised of a housing, said housing comprised of a polymeric material and an aqueous medium in contact with the housing, said aqueous medium comprised of (i) a drug or an electrolyte salt or a mixture thereof; (ii) propylene glycol; and (iii) an antimicrobial agent in an amount sufficient to inhibit microbial growth in the aqueous medium wherein the propylene glycol is present in an amount which renders the antimicrobial agent compatible with the device.

2. The transdermal electrotransport drug delivery or body analyte sampling device according to claim 1, wherein said aqueous medium has a pH in the range of about 4.0 to about 9.0.

3. The transdermal electrotransport drug delivery or body analyte sampling device according to claim 2, wherein said aqueous medium has a pH in the range of about 5.0 to about 8.0.

4. The transdermal electrotransport drug delivery or body analyte sampling device according to claim 1, wherein said aqueous medium comprises a buffer, a drug or an electrolyte salt or a mixture thereof, propylene glycol and an antimicrobial agent in an amount sufficient to inhibit microbial growth in the aqueous medium.

5. The transdermal electrotransport drug delivery or body analyte sampling device according to claim 1, wherein the polymeric housing material is selected from the group consisting of polyethylene terephthalate, polyethylene terephthalate modified with cyclohexane dimethylol, polypropylene, polyethylene, polyethylene copolymers, and mixtures thereof.

6. The transdermal electrotransport drug delivery or body analyte sampling device according to claim 1, wherein said reservoir is substantially drug free.

7. The transdermal electrotransport drug delivery or body analyte sampling device according to claim 1, wherein said anode includes an anodic electrode and an anodic reservoir, said anodic reservoir comprised of a polymeric housing, said anodic reservoir containing a drug.

8. The transdermal electrotransport drug delivery or body analyte sampling device according to claim 7, wherein said anodic reservoir contains a fentanyl-based active agent.

9. The transdermal electrotransport drug delivery or body analyte sampling device according to claim 1, wherein said antimicrobial agent is selected from the group consisting of methylparaben, ethylparaben and propylparaben, propyl gallate, butylated hydroxyanisole (BHA), butylated hydroxytoluene, t-butylhydroquinone, chloroxylenol, chlorohexidine, dichlorobenzyl alcohol, dehydroacetic acid, hexetidine and triclosan.

10. The transdermal electrotransport drug delivery or body analyte sampling device according to claim 1, wherein said antimicrobial agent is a paraben.

11. The transdermal electrotransport drug delivery or body analyte sampling device according to claim 1, wherein said antimicrobial agent is present in a concentration at least about 0.005% by weight.

12. The transdermal electrotransport drug delivery or body analyte sampling device according to claim 11, wherein said aqueous medium contains from about 0.005% by weight to about 2% by weight of said antimicrobial agent.

13. The transdermal electrotransport drug delivery or body analyte sampling device according to claim 12, wherein said aqueous medium contains from about 0.01% by weight to about 1% by weight of said antimicrobial agent.

14. The transdermal electrotransport drug delivery or body analyte sampling device according to claim 1, wherein said propylene glycol is present in a range of about 5% by weight to about 50% by weight.

15. The transdermal electrotransport drug delivery or body analyte sampling device according to claim 14, wherein said propylene glycol is present in a range of about 5% by weight to about 30% by weight.

16. The transdermal electrotransport drug delivery or body analyte sampling device according to claim 1, wherein the antimicrobial agent is one of substantially neutral in charge in the aqueous medium and has a charge that is not driven transdermally by the charge of the electrode in contact with the aqueous medium when in operation.

17. The transdermal electrotransport drug delivery or body analyte sampling device according to claim 16, wherein the antimicrobial agent in the aqueous medium is of a charge that is not driven transdermally by the charge of the electrode in contact with the aqueous medium when in operation.

18. The transdermal electrotransport drug delivery or body analyte sampling device according to claim 16, wherein the antimicrobial agent in the aqueous medium is of a charge that is not driven transdermally by the charge of the electrode in contact with the aqueous medium which is at pH from 5 to 8 when in operation, said propylene glycol is present in a range of 5% by weight to 30% by weight to render soluble said antimicrobial agent in a concentration of 0.005% to 2% by weight in the aqueous medium.

19. The transdermal electrotransport drug delivery or body analyte sampling device according to claim 16, wherein the antimicrobial agent in the aqueous medium is of a charge that is not driven transdermally by the charge of the electrode in contact with the aqueous medium which is at pH from 5 to 8 when in operation, said propylene glycol being present in a range of 5% by weight to 30% by weight to render soluble said antimicrobial agent in a concentration of 1% to 2% by weight in the aqueous medium.

20. A transdermal electrotransport drug delivery or body analyte sampling device, comprising: an anode; a cathode, at least one of said anode and cathode including an electrode and a reservoir comprised of a housing, said housing comprised of a polymeric material; a source of electrical power electrically connected to said anode and cathode; and an aqueous medium in contact with said housing, said aqueous medium comprised of a drug or an electrolyte salt or a mixture thereof, propylene glycol and an antimicrobial agent in an amount sufficient to inhibit microbial growth in the aqueous medium, wherein the propylene glycol is present in an amount which renders the antimicrobial agent compatible with the device and said antimicrobial agent is present in a concentration at least about 0.005% by weight.

21. A transdermal electrotransport drug delivery or body analyte sampling device, comprising: an anode; a cathode, at least one of said anode and cathode including an electrode and a reservoir comprised of a housing, said housing comprised of a polymeric material; a source of electrical power electrically connected to said anode and cathode; and an aqueous medium in contact with said housing, said aqueous medium comprised of a drug or an electrolyte salt or a mixture thereof, propylene glycol and an antimicrobial agent in an amount sufficient to inhibit microbial growth in the aqueous medium said antimicrobial agent being dissolved but is substantially neutral in charge in the presence of propylene glycol in the aqueous medium which is at pH from 5 to 8 when in operation.

\* \* \* \* \*